United States Patent [19]

Garito et al.

[11] Patent Number: 4,517,975

[45] Date of Patent: May 21, 1985

[54] ELECTROSURGICAL ELECTRODE FOR MATRISECTOMY

[76] Inventors: Jon C. Garito, 264 Hedge La., Hewlett Harbor, N.Y. 11577; Alan G. Ellman, 1 Auerbach La., Lawrence, N.Y. 11516

[21] Appl. No.: 501,408

[22] Filed: Jun. 6, 1983

[51] Int. Cl.³ .............................................. A61B 17/39
[52] U.S. Cl. .............................. 128/303.13; 219/234; 433/32
[58] Field of Search .................. 128/303.13–303.18, 128/355; 433/32; 219/233–235

[56] References Cited

U.S. PATENT DOCUMENTS

| | | | |
|---|---|---|---|
| 1,735,271 | 11/1929 | Groff | 128/303.14 |
| 1,794,296 | 2/1931 | Hyams | 128/303.14 |
| 2,012,316 | 8/1935 | Miles | 128/303.18 |
| 3,532,095 | 10/1970 | Miller et al. | 128/303.13 |
| 4,034,761 | 7/1977 | Prater et al. | 128/303.14 |
| 4,449,926 | 5/1984 | Weiss | 433/32 |

FOREIGN PATENT DOCUMENTS 2639157 3/1978 Fed. Rep. of Germany .................. 128/303.13

Primary Examiner—Lee S. Cohen

[57] ABSTRACT

A novel electrosurgical electrode tip with a spade-shaped end having one flat side coated with an insulating coating, especially adapted for a nail matrisectomy procedure.

8 Claims, 7 Drawing Figures

ELECTROSURGICAL ELECTRODE FOR MATRISECTOMY

This invention relates to novel electrosurgical electrodes, and in particular to electrosurgical electrodes for performing a nail matrisectomy.

BACKGROUND OF THE INVENTION

Electrosurgical procedures for humans and animals are well established in the medical and dental arts. The typical procedure involves generating a high frequency current, typically of the order of 2-4 MHz with a maximum output power of typically 50-150 Watts, and applying the current by way of an electrode to human or animal tissue. Different types of currents can be employed for different procedures. For example, fully rectified, fully filtered currents can be used for cutting tissue, fully rectified, non-filtered currents can be used for cutting with coagulation, partially rectified current can be used for hemostasis, and spark gap currents can be used for fulguration and dessication techniques. Such equipment is available from many suppliers. Various electrodes configurations are also available; for example, metal needles for making incisions, wire loops, round or diamond shaped, for planing and contouring tissue, balls for coagulation and hemostasis, and scalpel shapes for incisions and excision of tissue. In all these known electrode configurations, the working end is electrically conductive, usually metallic, and is fully exposed, so that all sides of the electrode working end are capable of transmitting the high frequency currents to the tissue.

Humans and animals can suffer from a condition commonly known as ingrown nail (hypertrophy of the unguia labia). The nail plate is rooted under a tissue fold at the digit proximal end and grows over a nail bed or matrix toward the distal end under lateral tissue folds in the so-called lateral grooves. The healthy nail should be rooted only at the proximal end. Ingrown nail results when the nail roots under the lateral folds. This results in laceration of the adjacent tissue, with possible pain, swelling and infection. The known surgical procedure, called matrisectomy, is to excise the unwanted or extraneous root. Merely removing the nail plate section adjacent the extraneous root will not prevent recurrence of the symptions; the entire extraneous root must be excised and precautions taken to prevent re-rooting of the nail along the lateral grooves. The nail lateral edges or margin fit snugly into the groove and normally there is a little less than 1 mm of space between the nail margin and the nail lateral wall or lip. Hence, the normal surgical procedure is to cut along the tissue edges bordering the nail groove in order to expose and excise the extraneous root.

BRIEF SUMMARY OF THIS INVENTION

An object of the invention is to provide an electrosurgical procedure for treating ingrown nail.

Another object of the invention is a novel electrosurgical electrode tip adapted for a matrisectomy procedure.

Still a further object of the invention is a novel electrosurgical electrode tip which enables an increase in electrosurgical procedures for humans and animals.

In accordance with the invention, these and other objects are achieved by a novel electrosurgery electrode tip whose working end is partly bare and partly insulated to selectively direct the electrosurgical current by way of the bare part to only part of the tissue with which the electrode tip is in contact or is adjacent. In a preferred form, the electrode tip is scalpel or spade shaped, one flat side of which is bare and the opposite flat side of which is coated with an electrical insulator. When such an electrode tip is contacted to tissue, the high frequency currents exit only via the bare electrode side. Tissue facing or contacting the coated side remains unexposed and unaffected by the high frequency currents.

DESCRIPTION OF THE DRAWINGS

The invention will now be described in greater detail with respect to several exemplary embodiments, taken in conjunction with the annexed drawings wherein.

DETAILED DESCRIPTION OF PREFERRED EMBODIMENTS

Figure 1A:
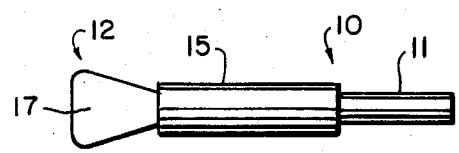
FIGS. 1A and 1B are plan and side views, respectively, of one form of electrosurgical electrode in accordance with the invention.
Figure 1B:
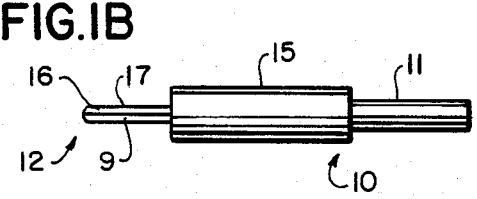

FIGS. 1A and 1B are plan and side views of one form of electrode 10 in accordance with the invention. It comprises an elongated one-piece metal body having at one end a cylindrical shank 11 and at the opposite end, the working end, a scalpel or spade shaped tip 12 with opposed flat sides. The shank 11 plugs into a standard handpiece 8 (partly shown in FIG. 2) connected to the electrosurgical apparatus, shown in dashed lines in FIG. 2 at 13. Typically, the part of the shank 11 that remains exposed after the electrode 10 is plugged into the handpiece 8 is enclosed with a cylindrical insulator jacket shown at 15. In the prior art known electrodes, the spade tip 12 is completely bare. In the invention, in contrast, one flat side is coated with an insulating coating 16. The bottom flat side 9 remains bare. Preferably, the shank 11 is constructed of malleable material so it is bendable and can be shaped by the practitioner into a desired configuration. Similarly, the spade tip 12 is preferable made of malleable material so it too is bendable in its plane and can be bent by the practitioner into a desired shape. As one example only, which is not to be considered limiting, the overall length of the electrode is 2⅜ inches, with a shank diameter of 1/16-3/32 inches. The spade tip is approximately 11 mm long, which widens from 1/16 inches wide at its proximal end to 4 mm wide at its distal end. The uncoated tip thickness 9 is approximately 0.01 in. thick, and the coating 16 has a thickness of about 0.004 in. Other shapes and thicknesses are also suitable. For matrisectomy, a suitable range of metal thickness is from about 0.006-0.050 in., and for the coating from 0.002-0.020 in. It is preferred to provide a family of four electrodes from the largest as above described down to the smallest having a maximum spade width of 1 mm, in 1 mm steps, with corresponding spade lengths of 5-11 mm. This is illustrated in FIGS. 3, with the width indicated by numeral 7.

The manufacture of the electrode uses conventional techniques with the addition of the coating 16 on one side of the spade tip 12. One starts with a rod of the shank diameter and the flattens and contours one end to form the spade tip. Any conductive material can be used, but metal is common. Typically brass, stainless steel, or titanium is employed. The brass is preferred because it can be readily obtained in malleable form. One side of the flattened spade end is then coated with a thin coating 16 of a suitable plastic resin. Acrylic resins are preferred. This is formed in a conventional way by obtaining liquid polymerisable resins or by mixing resin powders in a suitable diluent to form a liquid, painting a thin layer of the liquid resin onto one side of the electrode tip, and then heating or subjecting it to radiation to polymerize the coating. The powders are preferably colored or tinted so that the resultant coating 16 is colored differently from the bare metal 9 and is thus readily observable by the practitioner. Afterwards, a thin liquid glaze (not shown) may be applied or coated over the resin surface 16 to provide if needed a smooth protective surface 17. The smooth surface 17 facilitates placement of the electrode under the proximal nail fold 20 as will be later described. Other electrically insulating coatings can be substituted for the resin 16. The properties the coating resins preferably possess include good insulating-or dielectric properties to block flow of electrical currents to adjacent tissue, ability to bond well to the metal electrode tip, the ability to withstand sterilization as in a steam autoclave, which means resistance to oxidation or deterioration at temperatures up to 1200° F. and resistance to chemical corrosion, and preferably a resistance to sticking to tissue especially coagulated tissue. Such materials are well known in the medical field and include not only acrylics but also TEFLON, MYLAR (trademarked resin materials), epoxies and vinyls. Some materials such as TEFLON have a natural smooth non-stick surface and therefore will not require the extra glaze above described. Those that are not sufficiently smooth can always be lightly glazed. The resins chosen can be of the type which cold-cure or which require baking or other treatments to harden. The insulating coating, which is only on one side of the spade tip, may if desired be extended over the adjacent thin spade edges. As will be observed, the spade tip coating 16 extends up to the insulating jacket 15 on the shank.

Figure 2:
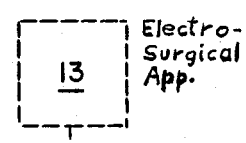
FIG. 2 is a partly schematic view ellustrating use of the electrode of FIG. 1 in a nail surgical procedure.
Figure 3:
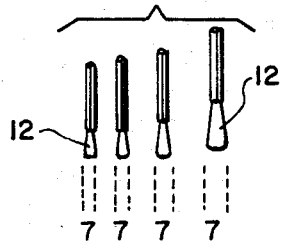
FIG. 3 illustrates a family of electrodes for various medical procedures.

FIG. 2 illustrates use of the electrode on a human or animal digit 25. The spade tip 12 is inserted under the tissue fold 26 covering the nail plate 27 edge until the bare bottom side 9 is located over the tissue section to be destroyed, designated in dashed lines by 29. When the equipment 13 is energized, after appropriate grounding of the patient, eg., to patient's calf, the high frequency currents flow through the bare bottom side 9 of the tip 12 and into the adjacent tissue 29. The operating conditions are chosen so as to destroy the cells adjacent the exposed electrode side 9. As one example, which is not to be considered limiting, power is applied for 1-2 seconds while moving electrode. Then, equipment is deenergized for 10-15 seconds, and power reapplied for 1-2 seconds if necessary and the procedure repeated until the extraneous root cells are destroyed. Using equipment available from Ellman International Manufacturing, known as the SURGITRON 90 F.F.P.F., it is recommended to use either the partially filtered or the fulguration current at about a 30 watt power level. Other currents and powers may be best with equipment from other suppliers, which is readily determined by simple experimentation. The tissue portions 26 abutting the upper coated side 16 of the spade tip 12 are unaffected by the high frequency currents. FIG. 2 also illustrates the advantages of the bendable shank 15 and tip 12. As will be noted, the shank has been bent at 23 to make it easier for the practitioner to insert the blade tip 12, which is also slight bent, under the nail fold 26.

Figure 4A:
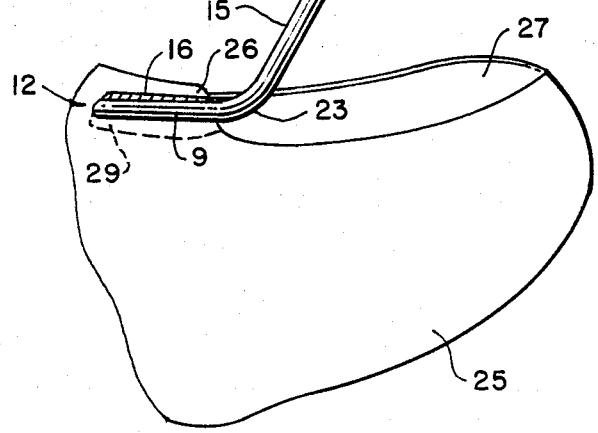
FIGS. 4A, 4B and 4C are three different views showing, schematically, placement of the electrode tip for a nail matrisectomy.
Figure 4A:
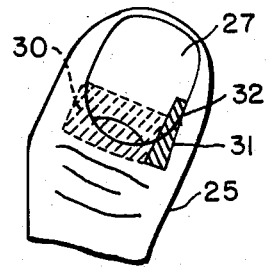
Figure 4B:
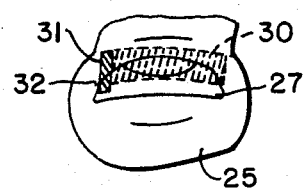
Figure 4C:
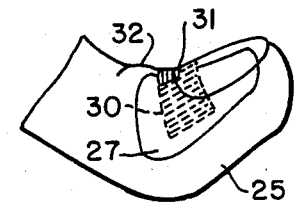

FIGS. 4A, 4B, and 4C are other schematic views illustrating use of the electrode in an electrosurgical partial matrisectomy procedure. The digit outline is again referenced 25, and the nail 27. The dashed rectangular section 30 indicates the nail matrix. The crosshatched section 31 indicates the electrode spade tip end (the shank is not shown for clarity). In the three figures, which are different views of the same procedure, the electrode end 31 is inserted, with coated side up, under a lateral nail fold 32, ie., in a lateral nail groove. When the equipment 13 is excited, the matrix cells underlying the exposed bottom side of the electrode are destroyed. The fold tissue 32 remains protected by the coating 16 and is unaffected. This allows complete destruction of any matrix sections where undesired rooting has occurred and thus complete destruction of the pathologic processes of the nail while avoiding longitudinal scalpel resection of the matrix, resulting in a shortened procedure accompanied by less bleeding and less likelihood of recurrence.

The partly insulated, partly bare electrode tip of the invention in the same or other configurations should also prove useful in other electrosurgical procedures for medical, dental or veternarian uses where the electrode tip is in contact with different tissues or tissue parts only some of which are to be selectively destroyed by currents from the bare part of the electrode tip while other contacted tissues or parts are to be preserved by the protective coating on the coated part of the electrode tip.

Also, other electrode tip configurations can be chosen to suit the medical procedure indicated. Still further, the invention is not limited to electrodes with a cylindrical shank. To mount within certain handpieces, the shank can be square or diamond shaped or have a screw end.

While our invention has been described in connection with specific embodiments thereof, those skilled in the art will recognize that various modifications are possible within the principles enunciated herein and thus the present invention is not to be limited to the specific embodiments disclosed.

What is claimed is:

1. An electrosurgical electrode comprising an elongate one-piece metal member having at one end means for mounting same in a handpiece and at the opposite end a working tip for delivering high frequency currents to animal tissue, said working tip having a thin flat spade-shaped end, and a thin insulating resin coating extending over one flat side of the spade-shaped end leaving the opposite side bare, said coating preventing transfer of high frequency currents to the tissue while allowing such transfer from the bare flat side, said metal member being constituted of a bendable malleable metal allowing bending of the member as well as of the tip by the user to adapt same to the tissue being treated.

2. The electrode of claim 1 wherein said one end comprises an elongated cylindrical shank portion of which the central part is enclosed with an insulating jacket, and the coating on said one flat side of the working tip extends up to the insulating jacket.

3. The electrode of claim 2 wherein the working tip has a slight outward taper.

4. The electrode of claim 1 wherein the spade shaped end has a thickness including the coating between about 0.008 and 0.070 inches and the spade width is between about 1 and 4 mm.

5. The electrode of claim 4 wherein the coating has a smooth outer surface and is constituted of an autoclavable plastic resin.

6. A medical procedure for partial or complete destruction of an animal nail matrix, comprising the steps of placing an electrosurgical spade shaped electrode with one insulatively coated side underneath the nail fold with the coated side up and with the bare bottom side over the matrix section whose cells are to be destroyed, and passing high frequency currents through the electrode until the matrix sections underlying its bare bottom side are destroyed while preserving tissue parts adjacent its coated side.

7. The procedure of claim 6 wherein the spade thickness including the coating is between about 0.008 and 0.070 inches, and the spade width is between about 1 and 4 mm.

8. The procedure of claim 7 wherein the electrode is constituted of bendable malleable metal, and the electrode is bent in order to facilitate placing same underneath the nail fold.

* * * * *